(12) United States Patent
Wang et al.

(10) Patent No.: US 11,571,145 B2
(45) Date of Patent: *Feb. 7, 2023

(54) HEART RATE DETECTION METHOD AND APPARATUS

(71) Applicant: Huawei Technologies Co., Ltd., Shenzhen (CN)

(72) Inventors: Huaiyong Wang, Xi'an (CN); Tao Yi, Shenzhen (CN); Xiangyang Wang, Xi'an (CN); Guangze Zhu, Xi'an (CN); Kui Zhang, Shenzhen (CN)

(73) Assignee: HUAWEI TECHNOLGOIES CO., LTD., Shenzhen (CN)

(*) Notice: Subject to any disclaimer, the term of this patent is extended or adjusted under 35 U.S.C. 154(b) by 342 days.

This patent is subject to a terminal disclaimer.

(21) Appl. No.: 16/881,838

(22) Filed: May 22, 2020

(65) Prior Publication Data

US 2020/0281507 A1 Sep. 10, 2020

Related U.S. Application Data

(63) Continuation of application No. 15/776,315, filed as application No. PCT/CN2016/098760 on Sep. 12, 2016, now Pat. No. 10,729,359.

(51) Int. Cl.
*A61B 5/11* (2006.01)
*A61B 5/024* (2006.01)
*A61B 5/00* (2006.01)

(52) U.S. Cl.
CPC ........ *A61B 5/1118* (2013.01); *A61B 5/02416* (2013.01); *A61B 5/02438* (2013.01);
(Continued)

(58) Field of Classification Search
None
See application file for complete search history.

(56) References Cited

U.S. PATENT DOCUMENTS 10,729,359 B2 * 8/2020 Wang ................. A61B 5/02438
2009/0156948 A1 6/2009 Shimizu et al.
(Continued)

FOREIGN PATENT DOCUMENTS

CN 101272731 A 9/2008
CN 101493865 A 7/2009
(Continued)

*Primary Examiner* — Ankit D Tejani
(74) *Attorney, Agent, or Firm* — Conley Rose, P.C.

(57) ABSTRACT

A heart rate detection method and an apparatus, where the method is applied to an electronic device, and the electronic device includes a heart rate sensor. The method includes detecting, by the electronic device, a current motion status of a user carrying the electronic device, determining, based on a prestored correspondence between a motion status, a startup period, and a sampling rate, a startup period and a sampling rate corresponding to the current motion status, where the startup period is a period in which the heart rate sensor is started to detect a heart rate of the user carrying the electronic device, and the sampling rate is a sampling rate of collecting heart rate data by the heart rate sensor, and starting the heart rate sensor at regular intervals based on the startup period to collect heart rate data at the sampling rate.

20 Claims, 3 Drawing Sheets

(52) U.S. Cl.
CPC .... *A61B 5/7285* (2013.01); *A61B 2560/0209* (2013.01); *A61B 2562/0219* (2013.01)

(56) References Cited

U.S. PATENT DOCUMENTS

| | | |
|---|---|---|
| 2012/0203076 A1 | 8/2012 | Fatta et al. |
| 2014/0118124 A1 | 5/2014 | Koyama |
| 2014/0243693 A1 | 8/2014 | Koyama et al. |
| 2014/0358472 A1 | 12/2014 | Goel et al. |
| 2015/0122018 A1 | 5/2015 | Yuen |
| 2015/0374310 A1 | 12/2015 | Lee |
| 2016/0015275 A1 | 1/2016 | Samadani et al. |
| 2016/0183880 A1 | 6/2016 | Abe |
| 2018/0020953 A1 | 1/2018 | Li et al. |

FOREIGN PATENT DOCUMENTS

| | | |
|---|---|---|
| CN | 103495263 A | 1/2014 |
| CN | 104323766 A | 2/2015 |
| CN | 104880941 A | 9/2015 |
| CN | 205019040 U | 2/2016 |
| CN | 105491948 A | 4/2016 |
| CN | 105496416 A | 4/2016 |
| CN | 105630172 A | 6/2016 |
| CN | 105726004 A | 7/2016 |
| CN | 105769143 A | 7/2016 |
| CN | 105832341 A | 8/2016 |
| CN | 106333667 A | 1/2017 |
| WO | 2016011318 A1 | 1/2016 |
| WO | 2016113143 A1 | 7/2016 |

* cited by examiner

HEART RATE DETECTION METHOD AND APPARATUS

CROSS-REFERENCE TO RELATED APPLICATIONS

This application is a continuation of U.S. patent application Ser. No. 15/776,315 filed on May 15, 2018, which is a U.S. National Stage of International Patent Application No. PCT/CN2016/098760 filed on Sep. 12, 2016. The disclosures of the aforementioned applications are hereby incorporated by reference in their entireties.

TECHNICAL FIELD

The present disclosure relates to the field of electronic technologies, and in particular, to a heart rate detection method and an apparatus.

BACKGROUND

All current intelligent electronic devices (such as smartwatches and smart bands) start to support real-time heart rate detection. In this case, a user carrying an intelligent electronic device can detect a heart rate change in real time during daily life or exercise to take exercise scientifically. However, a photoplethysmography (PPG) sensor is a device that consumes a significant amount of power. Keeping the sensor normally on greatly affects standby time of the device, affecting user experience of an intelligent electronic device. To resolve this problem a timing detection manner is used during real-time detection, for example, heart rate detection is started once every 10 minutes, that is, detection is started at regular intervals repeatedly, and a sampling rate of the sensor is fixed at a constant sampling rate.

The manner of starting a detector at regular intervals to detect a heart rate and performing sampling using a constant sampling rate cannot be used to accurately detect a heart rate condition of a user.

SUMMARY

Embodiments of the present disclosure provide a heart rate detection method and an apparatus to resolve a problem that a detector cannot accurately detect a heart rate condition of a user.

According to a first aspect, a real-time heart rate detection method is provided, where the method is applied to an electronic device, and the electronic device includes a heart rate sensor, and the method includes detecting, by the electronic device, a current motion status of a user carrying the electronic device, determining, by the electronic device based on a prestored correspondence between a motion status, a startup period, and a sampling rate, a startup period and a sampling rate corresponding to the current motion status, where the startup period is a period in which the heart rate sensor is started to detect a heart rate of the user carrying the electronic device, and the sampling rate is a sampling rate of collecting heart rate data by the heart rate sensor, and starting, by the electronic device, the heart rate sensor at regular intervals based on the startup period to collect heart rate data at the sampling rate.

According to the method provided in the present disclosure, a time of starting automatic heart rate detection and the sampling rate of detecting a heart rate by the heart rate sensor are determined based on the motion status of the user. This not only can ensure real-time performance of heart rate detection, but also can ensure continuity of data collected, thereby improving algorithm precision and saving power.

With reference to the first aspect, in a first possible implementation, detecting, by the electronic device, a current motion status of a user carrying the electronic device includes starting, by the electronic device based on a preset detection period, a motion sensor disposed in the electronic device to detect the current motion status of the user, where the detection period is a period in which the motion sensor is started to detect the motion status of the user.

With reference to the first aspect, in a second possible implementation, before determining a startup period and a sampling rate corresponding to the current motion status, the method further includes obtaining a stored historical motion status, where the historical motion status is prestored motion status information of the user, and comparing the current motion status with the historical motion status, and if the current motion status is different from the historical motion status, determining, based on the prestored correspondence between a motion status, a startup period, and a sampling rate, the startup period and the sampling rate corresponding to the current motion status.

In this implementation, before the heart rate sensor is adjusted, whether the motion status changes is determined. The heart rate sensor can be adjusted only when the motion status changes to reduce meaningless repeated operations on the heart rate sensor, and prolong service life of the heart rate sensor.

With reference to any one of the first aspect, or the first and the second possible implementations of the first aspect, in a third possible implementation, the prestored correspondence between a motion status, a startup period, and a sampling rate includes exercise intensity corresponding to the motion status is inversely proportional to the startup period, and the exercise intensity corresponding to the motion status is directly proportional to the sampling rate.

In this implementation, the detection period and the sampling rate of the heart rate sensor are adjusted based on a relationship between a motion status and a heart rate change, thereby improving detection precision and real-time performance of detection of the heart rate sensor.

According to a second aspect, a real-time heart rate detection apparatus is provided, and the apparatus further includes a detection unit configured to detect a current motion status of a user carrying the apparatus, a determining unit configured to determine, based on a prestored correspondence between a motion status, a startup period, and a sampling rate, a startup period and a sampling rate corresponding to the current motion status, where the startup period is a period in which the heart rate sensor of the apparatus is started to detect a heart rate of the user carrying the apparatus, and the sampling rate is a sampling rate of collecting heart rate data by the heart rate sensor, and an adjustment unit configured to start the heart rate sensor at regular intervals based on the startup period to collect heart rate data at the sampling rate.

With reference to the second aspect, in a first possible implementation, the detection unit is further configured to start, based on a preset detection period, a motion sensor disposed in the apparatus to detect the current motion status of the user, where the detection period is a period in which the motion sensor is started to detect the motion status of the user.

With reference to the second aspect, in a second possible implementation, the determining unit is further configured to obtain a stored historical motion status, where the historical motion status is prestored motion status information of the user, compare the current motion status with the historical motion status, and determine, based on the prestored correspondence between a motion status, a startup period, and a sampling rate, the startup period and the sampling rate corresponding to the current motion status if the current motion status is different from the historical motion status.

According to a third aspect, an electronic device is provided, including a heart rate sensor, a motion sensor, and a processor, where the heart rate sensor is configured to detect heart rate data of a user carrying the electronic device, the motion sensor is configured to detect a current motion status of the user carrying the electronic device, and the processor is configured to determine, based on a prestored correspondence between a motion status, a startup period, and a sampling rate, a startup period and a sampling rate corresponding to the current motion status, and start the heart rate sensor at regular intervals based on the startup period to collect heart rate data at the sampling rate, where the startup period is a period in which the heart rate sensor is started to detect a heart rate of the user carrying the electronic device, and the sampling rate is a sampling rate of collecting heart rate data by the heart rate sensor.

With reference to the third aspect, in a first possible implementation, the processor is further configured to start the motion sensor based on a preset detection period to detect the current motion status of the user, where the detection period is a period in which the motion sensor is started to detect the motion status of the user.

With reference to the third aspect, in a second possible implementation, the processor is further configured to obtain a stored historical motion status, compare the current motion status with the historical motion status, and determine, based on the prestored correspondence between a motion status, a startup period, and a sampling rate, the startup period and the sampling rate corresponding to the current motion status if the current motion status is different from the historical motion status, where the historical motion status is prestored motion status information of the user.

According to a fourth aspect, a computer-readable storage medium is provided, where the computer-readable storage medium stores program code that implements the real-time heart rate detection method described in the first aspect, and the program code includes an execution instruction used to execute the real-time heart rate detection method described in the first aspect.

One or two of the foregoing technical solutions have at least the following technical effects.

According to the solutions provided in the embodiments of the present disclosure, the motion status of the user is detected first based on a relationship between a motion status and a heart rate change, and starting real-time heart rate detection is further determined based on the motion status of the user. Because the heart rate of the user is closely related to the motion status, adjusting the startup period of heart rate detection based on the motion status can ensure that a heart rate detection frequency and a startup period meet a requirement of the user to the maximum extent, and can ensure real-time performance of heart rate detection and continuity of collected data, thereby improving algorithm precision.

DESCRIPTION OF EMBODIMENTS

The following describes the embodiments of the present disclosure in detail with reference to the accompanying drawings of the specification.

A heart rate change is closely related to a motion status of a person. A heart rate is quite stable when a user is in a sleeping or static state, and in this case, heart rate detection may be periodically performed on the user based on a first startup period and a first sampling rate. The heart rate change is relatively slow when the user is walking, and in this case, heart rate detection may be periodically performed on the user based on a second startup period and a second sampling rate. When the user is running, relatively strenuous exercise is taken, and the heart rate change is relatively fast. In this case, heart rate detection may be periodically performed on the user based on a third startup period and a third sampling rate. The heart rate change is detected to remind and instruct the user. The first startup period is longer than the second startup period, and the second startup period is longer than the third startup period. In addition, with a motion status change, a quantity of heart beats per minute changes with a motion status. For example, when the user is running, more strenuous exercise is taken, and the heart speeds up. To detect the heart rate accurately, the sampling rate may be adaptively adjusted based on different motion statuses of the user, to make the third sampling rate greater than the second sampling rate, and the second sampling rate greater than the first sampling rate. The following further describes in detail a method provided in the embodiments of the present disclosure according to the implementation principles.

Embodiment 1

Figure 1:
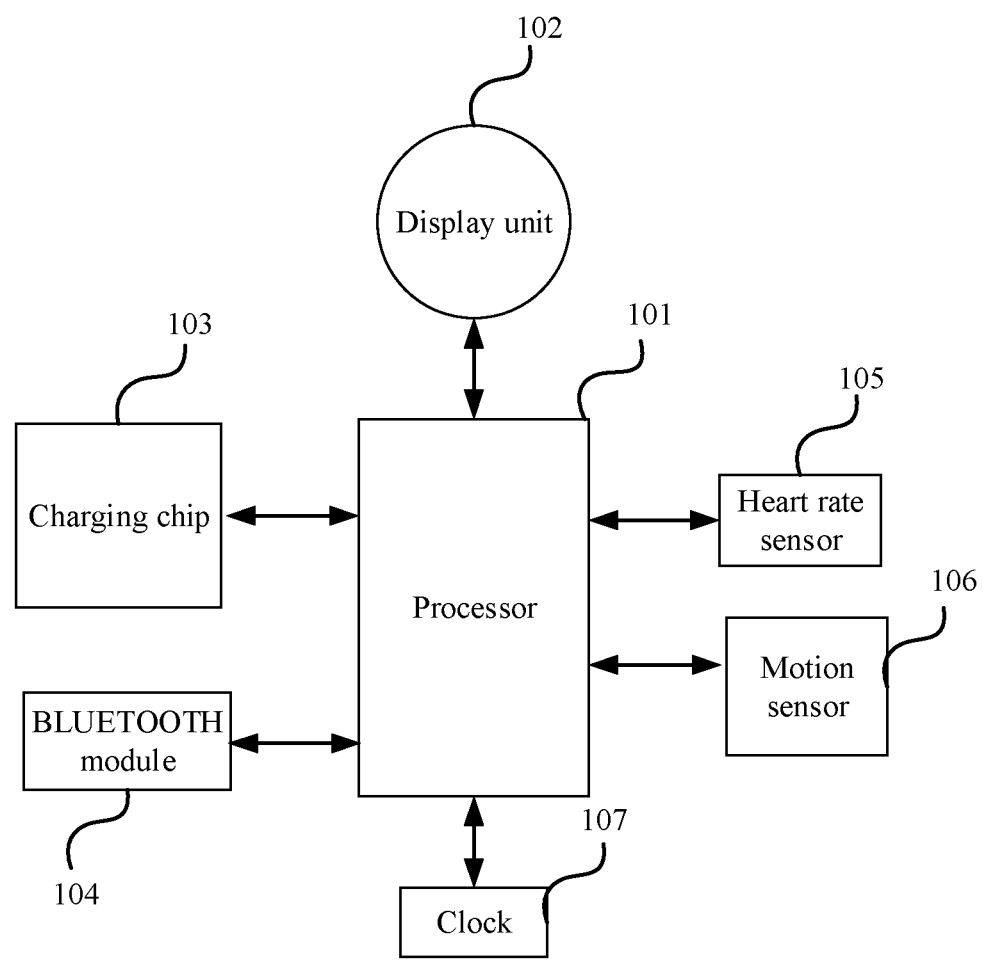
FIG. 1 is a schematic structural diagram of an electronic device according to an embodiment of the present disclosure.

As shown in FIG. 1, this embodiment of the present disclosure provides an electronic device. The electronic device includes a processor 101, a display unit 102, a charging chip 103, a BLUETOOTH module 104, a heart rate sensor 105, a motion sensor 106, and a clock 107.

The display unit 102 implements displaying of output content of the electronic device, and may be a liquid crystal display (LCD) screen in this embodiment.

The charging chip 103 implements charging management of the electronic device.

The BLUETOOTH module 104 implements communication between the electronic device and another electronic device.

The heart rate sensor 105 is configured to collect, during heart rate detection, data about a vascular change that varies with pulse of a user in order to calculate a heart rate value using a heart rate algorithm.

Optionally, the heart rate sensor 105 may include a control chip that implements the heart rate algorithm, a PPG sensor, an acceleration transducer (ACC), and the like.

The motion sensor 106 is configured to collect an acceleration value along a three-axis direction during motion of the user, and determine a current motion status of the user based on the acceleration value.

In the solution provided in this embodiment of the present disclosure, the processor 101 is configured to determine, based on a prestored correspondence between a motion status, a startup period, and a sampling rate, a startup period and a sampling rate corresponding to the current motion status, and start the heart rate sensor 105 at regular intervals based on the startup period to collect heart rate data at the sampling rate. The startup period is a period in which the heart rate sensor 105 is started to detect a heart rate of the user carrying the electronic device, and the sampling rate is a sampling rate of collecting heart rate data by the heart rate sensor 105.

Optionally, the processor 101 is further configured to start the motion sensor 106 based on a preset detection period to detect the current motion status of the user. The detection period is a period in which the motion sensor 106 is started to detect the motion status of the user.

In a manner provided in this embodiment, the motion sensor 106 may be started periodically based on the preset detection period, reducing unnecessary energy consumption caused by the motion sensor 106 being always on. The detection period may be properly set based on specific needs.

Optionally, the processor 101 is further configured to obtain a stored historical motion status, compare the current motion status with the historical motion status, and determine, based on the prestored correspondence between a motion status, a startup period, and a sampling rate, the startup period and the sampling rate corresponding to the current motion status if the current motion status is different from the historical motion status. The historical motion status is prestored motion status information of the user.

In a manner provided in this embodiment, the startup period and the sampling rate are merely adjusted when it is determined that the currently detected motion status is different from the historical motion status (the historical motion status may be motion status information obtained through a previous motion status detection). This can reduce unnecessary operations on the heart rate sensor 105 and prolong service life of the heart rate sensor 105. If the current detection is a first motion status detection, it is directly determined that the current motion status is different from the historical motion status.

In this embodiment of the present disclosure, different startup periods and different sampling rates are used based on different motion statuses to monitor heart rate data, therefore, a heart rate is closely related to a motion status. In this embodiment, the prestored correspondence between a motion status, a startup period, and a sampling rate may be as follows.

Exercise intensity corresponding to the motion status is inversely proportional to a time interval of a detection period, and the exercise intensity corresponding to the motion status is directly proportional to the sampling rate.

According to the solution provided in this embodiment of the present disclosure, a time of starting automatic heart rate detection and the sampling rate of detecting the heart rate by the heart rate sensor 105 are determined based on the motion status of the user.

For example, when a user is sleeping or static, the user's heart rate is detected once an hour, and the sampling rate is set to 25 hertz (Hz), when the user is walking, the user's heart rate is detected once 30 minutes, and the sampling rate is set to 50 Hz, and when the user is running, the user's heart rate is detected once 10 minutes, and the sampling rate is set to 100 Hz.

Embodiment 2

Figure 2:
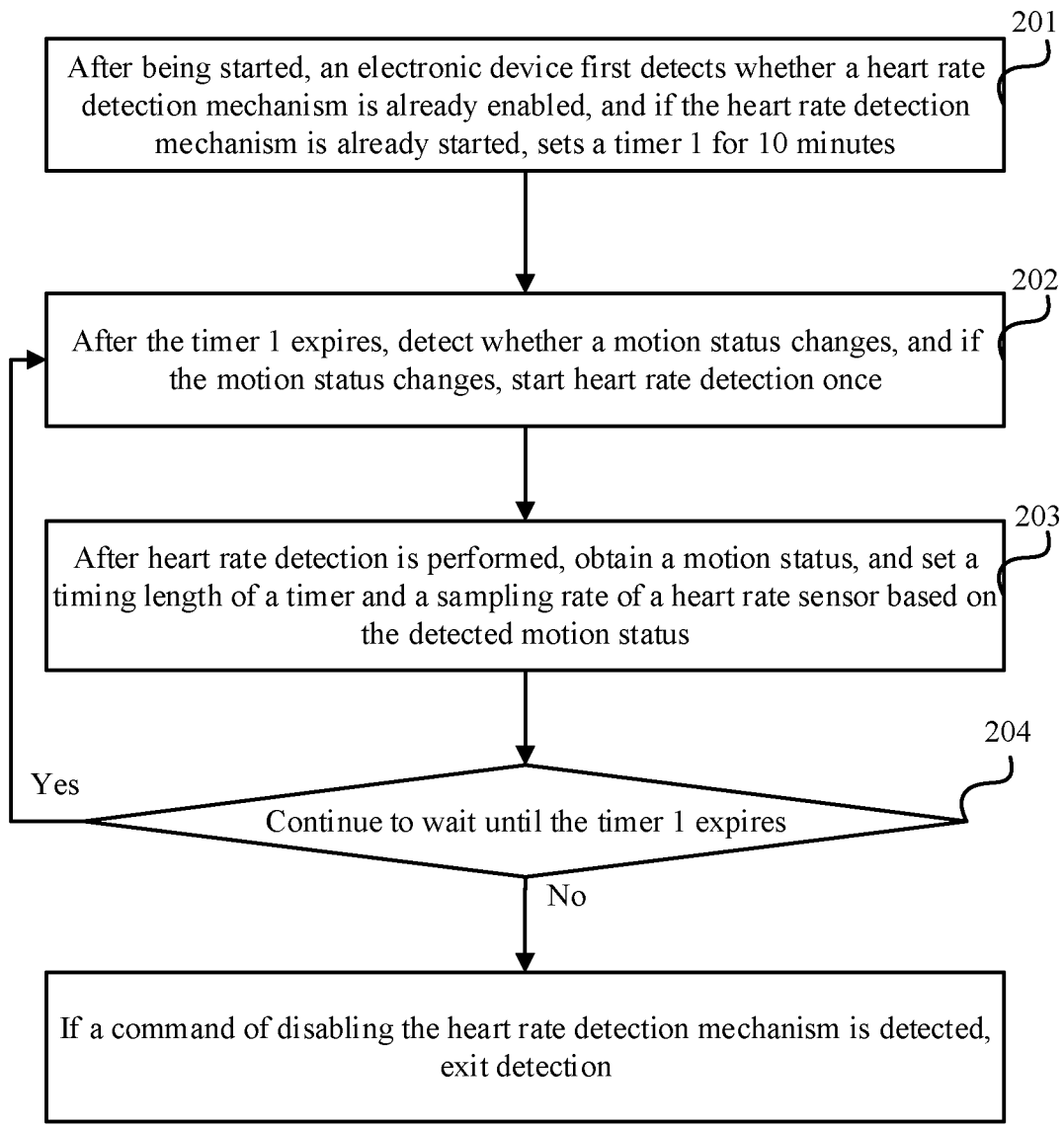
FIG. 2 is a schematic flowchart of a real-time heart rate detection method according to Embodiment 2 of the present disclosure.

As shown in FIG. 2, with reference to a specific application environment, a specific implementation of a real-time heart rate detection method provided in this embodiment of the present disclosure may be implemented in the following specific steps.

Step 201: After being started, an electronic device first detects whether a heart rate detection mechanism is already enabled, and if the heart rate detection mechanism is already enabled, may set a timer 1 for 10 minutes, where a sampling rate of a heart rate sensor (which may be a PPG sensor) is set to 100 Hz.

In this embodiment, after enabling the heart rate detection mechanism, the electronic device cannot determine a specific period length of the current heart rate detection. If a time interval of a fixed heart rate detection period is quite long, the electronic device needs to wait for a long period to perform next heart rate detection. Therefore, to make the heart rate detection period more proper, a timer 1 may be set in advance, and the electronic device may directly perform heart rate detection once based on the timer, and enable a corresponding motion detection mechanism.

Step 202: After the timer 1 expires, detect whether a motion status changes (if heart rate detection is triggered for the first time, it is determined that the motion status has changed), and if the motion status changes, start heart rate detection once and go to step 203.

In this embodiment, the timer is related to the startup period in which the electronic device starts the heart rate sensor. The following provides two optimal manners of setting the timer. Details may be as follows.

A: The electronic device adjusts parameter values of the timer 1 in real time based on different motion statuses. For example, if a current exercise intensity of a user is high, a timing length of the timer is short, if the exercise intensity is low, a length is long.

B: The electronic device sets two timers, a timer 1 and a timer 2, where the timer 1 is set for a fixed timing length, for example, 10 minutes, and time lengths of the timer 2 are in a one-to-one correspondence to motion statuses of a user, and for setting the timer 2, refer to examples shown in Table 1 (Values provided in Table 1 are only examples used to describe the solution of this embodiment, and do not limit that the timing length in this embodiment of the present disclosure can be only values shown in Table 1).

TABLE 1

| Motion status of a user | Time length of a timer 2 | Sampling rate |
|---|---|---|
| Sleeping/Static | 1 hour | 25 Hz |
| Walking | 30 minutes | 50 Hz |
| Running/Riding | 10 minutes | 100 Hz |

In this embodiment, both a PPG sensor and an ACC sensor may be used in a combined manner to collect a parameter related to a user's motion, and a motion status of a user is determined based on a preset heart rate algorithm and a status identification algorithm using the collected parameter.

Step 203: After heart rate detection is performed, obtain a motion status, and set a timing length of a timer and a sampling rate of a heart rate sensor based on the detected motion status.

In this embodiment, based on a quantity of timers in a specific example, when a timing length of a timer is set, a timing length of a timer 1 or a timer 2 is set accordingly.

Step 204: Continue to wait until the timer 1 expires, if the timer 1 expires, go to step 202, or if the timer 1 does not expire, continue to wait, and if a command of disabling the heart rate detection mechanism is detected, exit detection.

Embodiment 3

Figure 3:
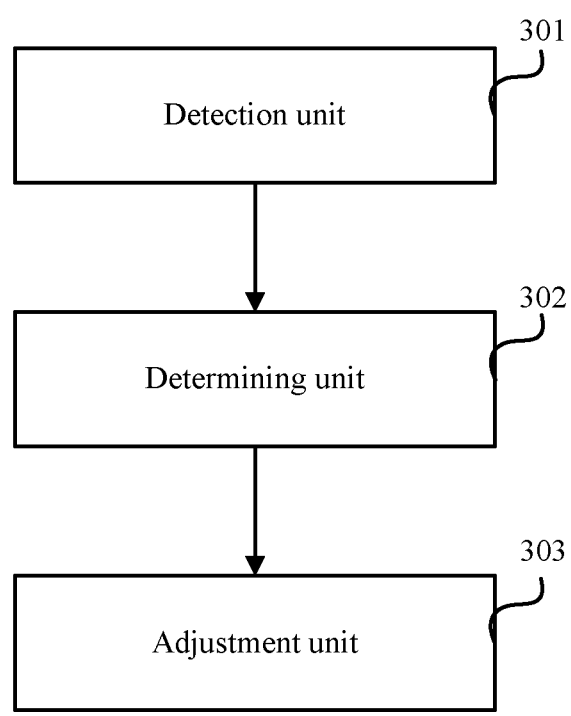
FIG. 3 is a schematic structural diagram of a real-time heart rate detection apparatus according to Embodiment 3 of the present disclosure.

As shown in FIG. 3, in order to implement the method provided in Embodiment 2, an embodiment of the present disclosure further provides a real-time heart rate detection apparatus. The apparatus includes a detection unit 301, a determining unit 302, and an adjustment unit 303.

The detection unit 301 is configured to detect a current motion status of a user carrying the apparatus.

Optionally, the detection unit 301 is further configured to start, based on a preset detection period, a motion sensor disposed in the apparatus to detect the current motion status of the user. The detection period is a period in which the motion sensor is started to detect the motion status of the user.

The determining unit 302 is configured to determine, based on a prestored correspondence between a motion status, a startup period, and a sampling rate, a startup period and a sampling rate corresponding to the current motion status. The startup period is a period in which the heart rate sensor of the apparatus is started to detect a heart rate of the user carrying the apparatus, and the sampling rate is a sampling rate of collecting heart rate data by the heart rate sensor.

Optionally, the determining unit 302 is further configured to obtain a stored historical motion status, where the historical motion status is prestored motion status information of the user, compare the current motion status with the historical motion status, and determine, based on the prestored correspondence between a motion status, a startup period, and a sampling rate, the startup period and the sampling rate corresponding to the current motion status if the current motion status is different from the historical motion status.

The adjustment unit 303 is configured to start the heart rate sensor at regular intervals based on the startup period to collect heart rate data at the sampling rate.

The foregoing technical solutions provided in the embodiments of this application have at least the following technical effects or advantages.

In the method and the apparatus provided in the embodiments of the present disclosure, a time of starting automatic heart rate detection and the sampling rate of detecting a heart rate by the heart rate sensor are determined based on the motion status of the user. This not only can ensure real-time performance of heart rate detection, but also can ensure continuity of data collected, thereby improving algorithm precision and saving power.

The present disclosure is described with reference to the flowcharts and/or block diagrams of the method, the device (system), and the computer program product according to the embodiments of the present disclosure. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of any other programmable data processing device to generate a machine such that the instructions executed by a computer or a processor of any other programmable data processing device generate an apparatus for implementing a specific function in one or more processes in the flowcharts and/or in one or more blocks in the block diagrams.

These computer program instructions may be stored in a computer readable memory that can instruct the computer or any other programmable data processing device to work in a specific manner such that the instructions stored in the computer readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing device such that a series of operations and steps are performed on the computer or the other programmable device, thereby generating computer-implemented processing. Therefore, the instructions executed on the computer or the other programmable device provides steps for implementing a specific function in one or more processes in the flowcharts and/or in one or more blocks in the block diagrams.

Obviously, a person skilled in the art can make various modifications and variations to the present disclosure without departing from the spirit and scope of the present disclosure. The present disclosure is intended to cover these modifications and variations provided that they fall within the scope of protection defined by the following claims and their equivalent technologies.

What is claimed is:

1. A heart rate detection method applied to an electronic device comprising a heart rate sensor, wherein the heart rate detection method comprises:
    detecting a current motion status of a user carrying the electronic device;
    obtaining based on a prestored correspondence among a motion status, a startup period, and a sampling rate, a first startup period and a first sampling rate corresponding to the current motion status, wherein the first startup period comprises a period in which the heart rate sensor starts to detect a heart rate of the user carrying the electronic device, wherein the first sampling rate comprises a sampling rate of collecting heart rate data by the heart rate sensor, wherein the prestored correspondence comprises exercise intensity corresponding to the motion status, and wherein the exercise intensity is inversely proportional to the startup period and is directly proportional to the sampling rate; and
    starting the heart rate sensor at regular intervals based on the first startup period to collect the heart rate data at the first sampling rate.

2. The heart rate detection method of claim 1, further comprising starting, based on a preset detection period, a motion sensor disposed in the electronic device to detect the current motion status of the user, wherein the preset detection period comprises a period in which the motion sensor starts to detect the motion status of the user.

3. The heart rate detection method of claim 2, further comprising starting the motion sensor periodically based on the preset detection period.

4. The heart rate detection method of claim 2, further comprising starting the motion sensor periodically based on the preset detection period.

5. The method of claim 2, wherein the preset detection period and the sampling rate of the heart rate sensor are adjusted based on a relationship between the motion status and a heart rate change.

6. The heart rate detection method of claim 1, wherein before determining the first startup period and the first sampling rate corresponding to the current motion status, the heart rate detection method further comprises:
obtaining a stored historical motion status comprising prestored motion status information of the user;
comparing the current motion status with the stored historical motion status; and
determining, based on the prestored correspondence, the first startup period and the first sampling rate corresponding to the current motion status when the current motion status is different from the stored historical motion status.

7. The heart rate detection method of claim 1, further comprising periodically collecting the heart rate data during a static motion status of the user based on the first startup period and the first sampling rate.

8. The heart rate detection method of claim 1, wherein the heart rate sensor comprises a photoplethysmography (PPG) sensor or an acceleration transducer (ACC).

9. A computer program product comprising computer-executable instructions stored on a non-transitory computer-readable medium that, when executed by a processor, cause a real-time heart rate detection apparatus to:
detect a current motion status of a user carrying the heart rate detection apparatus;
obtain, based on a prestored correspondence among a motion status, a startup period, and a sampling rate, a first startup period and a first sampling rate corresponding to the current motion status, wherein the first startup period comprises a period in which a heart rate sensor of the heart rate detection apparatus starts to detect a heart rate of the user carrying the heart rate detection apparatus, wherein the sampling rate comprises a sampling rate of collecting heart rate data by the heart rate sensor, wherein the prestored correspondence comprises exercise intensity corresponding to the motion status, and wherein the exercise intensity is inversely proportional to the startup period and is directly proportional to the sampling rate; and
start the heart rate sensor at regular intervals based on the first startup period to collect the heart rate data at the first sampling rate.

10. The computer program product of claim 9, wherein the computer-executable instructions further cause the heart rate detection apparatus to start, based on a preset detection period, a motion sensor disposed in the heart rate detection apparatus to detect the current motion status of the user, and wherein the preset detection period comprises a period in which the motion sensor starts to detect the motion status of the user.

11. The computer program product of claim 10, wherein the computer-executable instructions further cause the heart rate detection apparatus to start the motion sensor periodically based on the preset detection period.

12. The computer program product of claim 9, wherein the computer-executable instructions further cause the heart rate detection apparatus to:
obtain a stored historical motion status, wherein the stored historical motion status comprises prestored motion status information of the user;
compare the current motion status with the stored historical motion status; and
determine, based on the prestored correspondence, the first startup period and the first sampling rate that are corresponding to the current motion status when the current motion status is different from the stored historical motion status.

13. The computer program product of claim 9, wherein the heart rate sensor comprises a photoplethysmography (PPG) sensor or an acceleration transducer (ACC).

14. The computer program product of claim 9, wherein the computer-executable instructions further cause the heart rate detection apparatus to periodically collect the heart rate data during a static motion status of the user based on the first startup period and the first sampling rate.

15. An electronic device, comprising:
a heart rate sensor configured to detect heart rate data of a user carrying the electronic device;
a motion sensor coupled to the heart rate sensor and configured to detect a current motion status of the user carrying the electronic device; and
a processor coupled to the heart rate sensor and motion sensor and configured to:
obtain, based on a prestored correspondence among a motion status, a startup period, and a sampling rate, a first startup period and a first sampling rate corresponding to the current motion status, wherein the prestored correspondence comprises exercise intensity corresponding to the motion status, and wherein the exercise intensity is inversely proportional to the startup period and is directly proportional to the sampling rate; and
start the heart rate sensor at regular intervals based on the first startup period to collect the heart rate data at the first sampling rate, wherein the first startup period comprises a period in which the heart rate sensor starts to detect a heart rate of the user carrying the electronic device, and wherein the first sampling rate comprises a sampling rate of collecting the heart rate data by the heart rate sensor.

16. The electronic device of claim 15, wherein the processor is further configured to start the motion sensor based on a preset detection period to detect the current motion status of the user, and wherein the preset detection period comprises a period in which the motion sensor starts to detect the motion status of the user.

17. The electronic device of claim 16, wherein the processor is further configured to start the motion sensor periodically based on the preset detection period.

18. The electronic device of claim 15, wherein the processor is further configured to:
obtain a stored historical motion status;
compare the current motion status with the stored historical motion status; and
determine, based on the prestored correspondence, the first startup period and the first sampling rate corresponding to the current motion status when the current motion status is different from the stored historical motion status, and wherein the stored historical motion status comprises prestored motion status information of the user.

19. The electronic device of claim 15, wherein the heart rate sensor is further configured to periodically collect the heart rate data during a static motion status of the user based on the first startup period and the first sampling rate.

20. The electronic device of claim 15, wherein the heart rate sensor comprises a photoplethysmography (PPG) sensor or an acceleration transducer (ACC).

* * * * *